United States Patent [19] | [11] Patent Number: 4,911,098
Tabata | [45] Date of Patent: Mar. 27, 1990

[54] AUTOMATIC STRAINING APPARATUS FOR SLIDE SPECIMENS

[75] Inventor: Yoshio Tabata, Tokyo, Japan

[73] Assignee: Shiraimatsu & Co., Ltd., Osaka, Japan

[21] Appl. No.: 266,570

[22] Filed: Nov. 3, 1988

[30] Foreign Application Priority Data

Dec. 28, 1987 [JP] Japan ................................. 62-334925
Dec. 28, 1987 [JP] Japan ................................. 62-334926

[51] Int. Cl.$^4$ .......................... B05C 13/00; B05C 3/02
[52] U.S. Cl. .................................... 118/423; 118/500; 901/31
[58] Field of Search ............... 118/423, 682, 684, 500; 901/31, 37, 38

[56] References Cited

U.S. PATENT DOCUMENTS 3,507,292  4/1970  Pedersen ............................. 118/423
3,837,795  9/1974  Becker et al. ....................... 118/423
4,200,056  4/1980  Johnson ............................. 118/423

Primary Examiner—Willard Hoag
Attorney, Agent, or Firm—Darby & Darby

[57] ABSTRACT

This invention relates to an automatic staining apparatus for staining many slide specimens such as tissue specimens by dipping them sequentially into a large number of chemical solution containers while they are mounted in a slide holder basket.

Conventional automatic staining apparatuses have a problem in the staining efficiency because a basket is attached manually to a clamp member of the apparatus, and also have another problem that remaining chemical solution cannot be sufficiently removed from slide specimens.

In order to solve these problems, an automatic staining apparatus according to the first present invention has the clamp member which can automatically engage with, and disengage from a basket, so that the staining efficiency is much improved. Preferred embodiment of the invention has a tilting mechanism for the clamp member, so that chemical solution is sufficiently removed from slide specimens.

Another automatic staining apparatus according to the second invention has n (an integer of 2 or more) clamp members, each of which is characterized by the same as the first invention, and (n−1) relay stations inside the apparatus, so that a basket can be relayed automatically from one clamp member to another inside the apparatus and staining can be carried out for maximum n baskets at same time and independently from each other. Therefore, the rate of operation of staining apparatus is substantially maximum n-times. Preferred embodiments of the second invention also has a tilting mechanism for each clamp member, so that chemical solution is sufficiently removed.

39 Claims, 7 Drawing Sheets

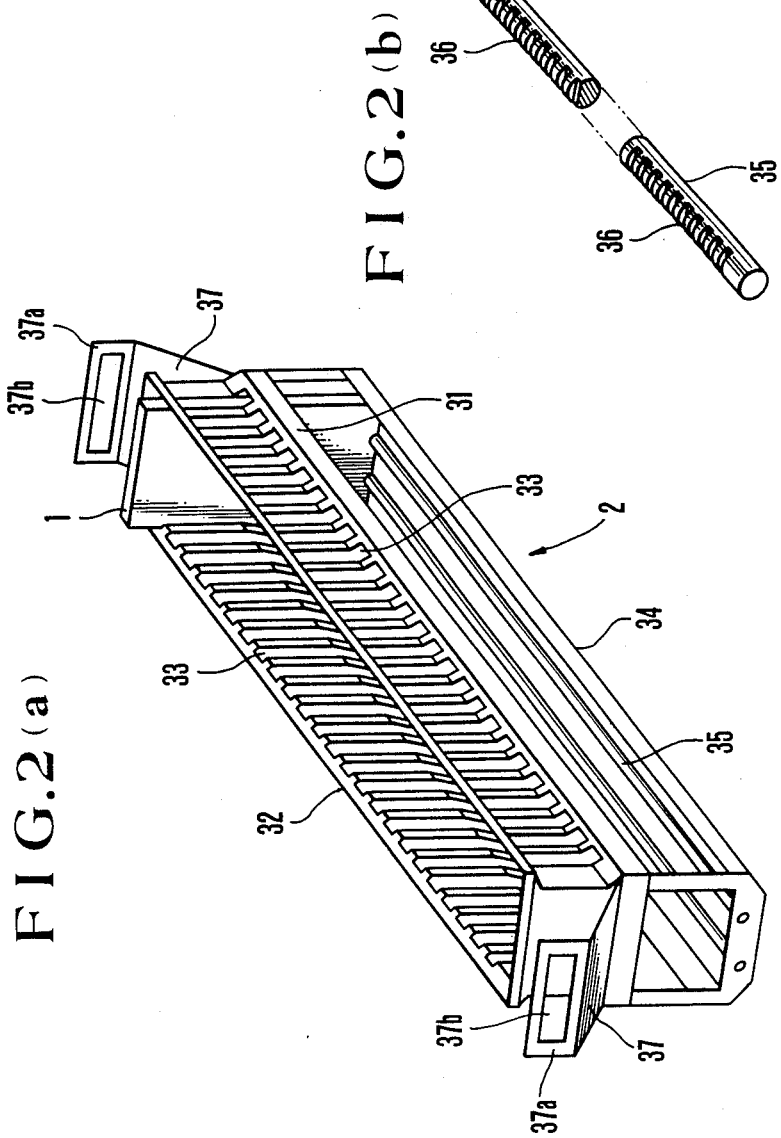

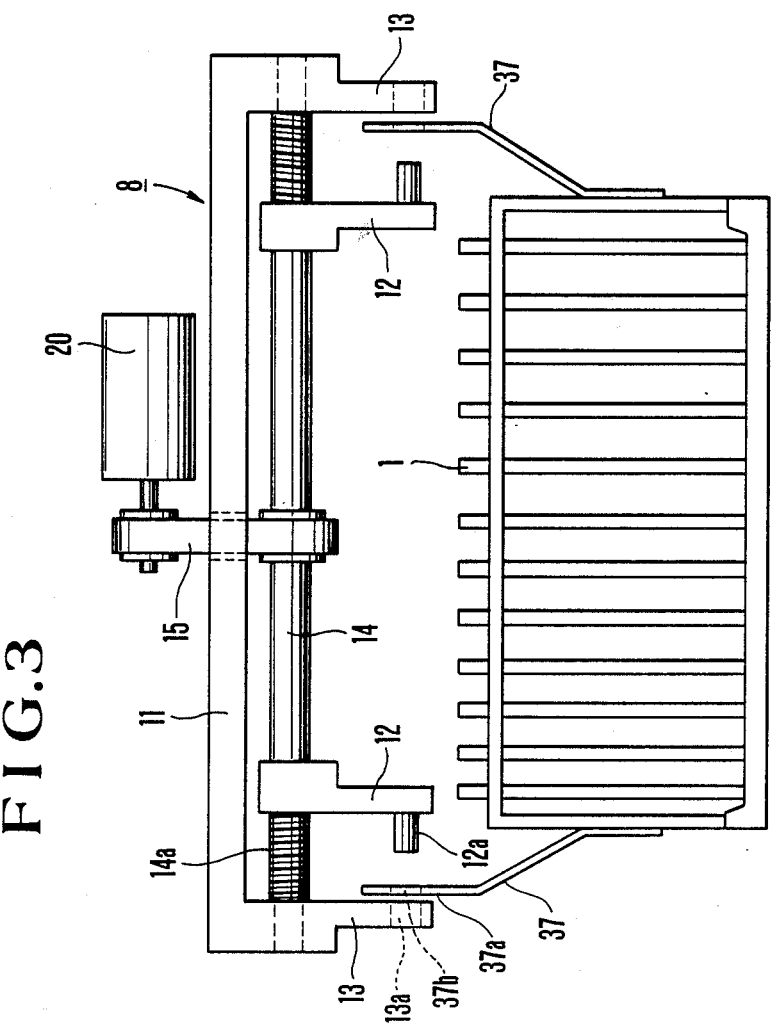

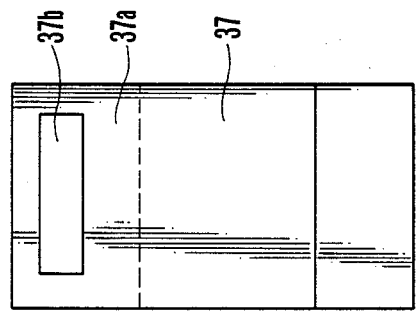
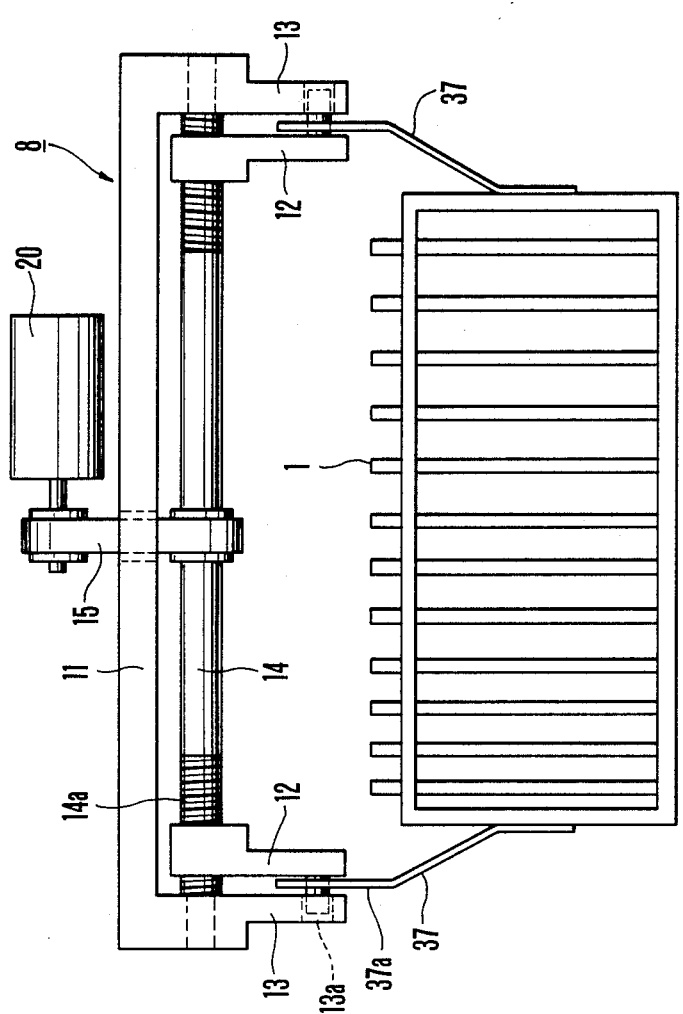

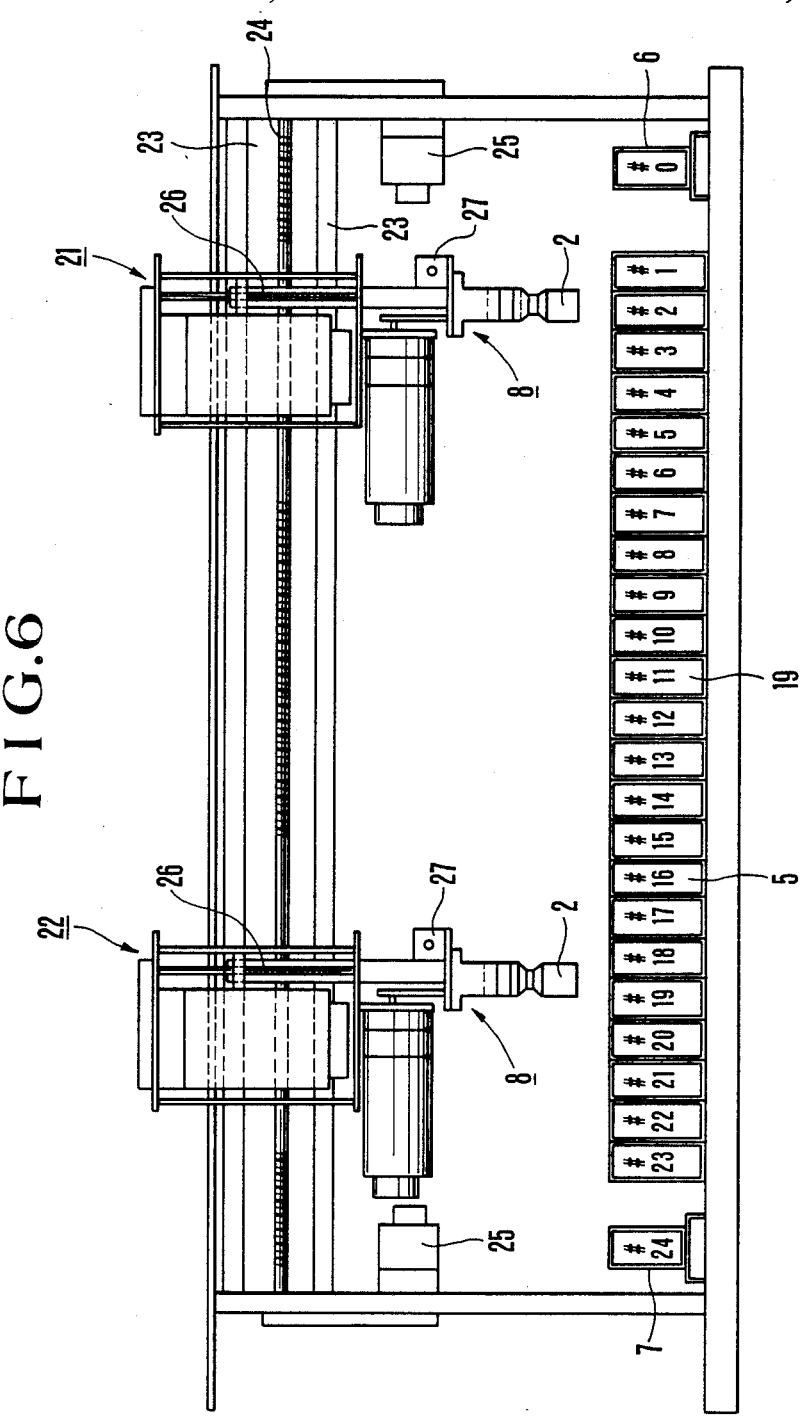

AUTOMATIC STRAINING APPARATUS FOR SLIDE SPECIMENS

BACKGROUND OF THE INVENTION

1. Field of the Invention

This invention relates to an automatic staining apparatus used in the staining step of slide specimens such as tissue specimens, cytodiagnostic specimens, and the like. More particularly, the present invention relates to a clamp member of the automatic staining apparatus and a slide holder basket which engages with the clamp member and stores therein slide glass specimens.

2. Description of the Related Art

Slide specimens such as tissue specimens, cytodiagnostic specimens, etc. are prepared by the following steps.

(1) A step of cutting the tissue or the like into a slice, extending the slice uniformly on a slide glass to bring the slice into close contact with the glass, thus preparing primary slide specimen.

(2) A step of staining the primary slide glass specimen with a specified chemical solution such as hematoxylin solution, eosin solution, Papanicolaou solution, May-Giemsa solution, or Wright-Giemsa solution in accordance with the object of the slide specimen to prepare a secondary slide specimen.

Table 1 below shows the typical procedures of H.E. (hematoxylin-eosin) staining of human tissue specimens.

TABLE 1

Procedures of H. E. Staining of Human Tissue Specimens

| Step | Time | Chemical solution |
|---|---|---|
| 1 | 1 min | xylene (1) |
| 2 | 1 min | xylene (2) |
| 3 | 3 sec | alcohol (1) |
| 4 | 3 sec | alcohol (2) |
| 5 | 3 sec | alcohol (3) |
| 6 | 2 min 3 sec | washing with running water |
| 7 | 3 min | distilled water (1) |
| 8 | 5 min | Carazzi hematoxylin |
| 9 | 2 min | washing with running water |
| 10 | 3 min | distilled water (2) |
| 11 | 3 sec | HCl-alcohol |
| 12 | 2 min | washing with running water |
| 13 | 3 min | distilled water (3) |
| 14 | 10 sec | 80% alcohol |
| 15 | 10 sec | 80% alcohol |
| 16 | 1 min | eosin |
| 17 | 8 min | washing with running water |
| 18 | 3 min | distilled water (4) |
| 19 | 30 sec | alcohol (4) |
| 20 | 30 sec | alcohol (5) |
| 21 | 30 sec | alcohol (6) |
| 22 | 1 min | xylene (3) |
| 23 | 1 min | xylene (4) |
| 24 |  | end |

(3) A sealing step of causing an ordinary sealing medium to flow on the cell, tissue, etc. of the secondary slide specimen prepared in the staining step and putting a cover glass on it to prepare a final slide glass specimen.

A conventional automatic staining apparatus used in the staining step described above is shown in FIG. 7.

In order to stain a large number of the primary slide glass specimens at the same time, a staining slide holder basket 2 (the conventional straining slide holder basket is shown schematically in FIG. 8) is constructed so as to mount a large number of slide glasses 1. At times, staining is carried out while two such baskets are aligned side by side. Staining is carried out while the handle 3 of the basket is hooked on a clamp member 4 of the staining apparatus. This clamp member 4 is attached to the basket 2 manually at the basket attaching position of the staining apparatus and removed manually at the basket removing position. While the handle of the basket is hooked on the clamp member of the staining apparatus, the clamp member is moved both transversely and longitudinally and positioned on a specified chemical solution container 5. Next, the clamp member 4 is lowered and the primary slide specimens 1 mounted in the basket 2 are dipped into the chemical solution for a given period. Thereafter, the clamp member is moved up. The basket is shaken up and down while the primary slide specimens are dipped into the chemical solution in order to effect uniform chemical solution treatment.

The staining has been carried out by repeating the procedures described above.

However, the conventional staining apparatus involves the following problems.

Problem (1)

Conventionally the staining slide holder basket has been attached manually to the clamp member of the automatic staining apparatus. In other words, an operator attaches the staining slide holder basket when the clamp member arrives at the basket attaching position and removes it when the clamp member arrives at the removing position. Therefore, the waiting time is required for the attaching and removing operations by the operator and the efficiency of staining is low.

Problem (2)

Since the basket has been manually attached to and removed from the clamp member, it has not been possible to automatically attach and remove the basket at the intermediate stage of the staining or inside the staining apparatus. Accordingly, the number of clamp members is generally one and the hourly rate of staining work is low. Particularly when the number of steps of staining is increased, this problem becomes all the more critical.

Problem (3)

After the chemical solution treatment, the basket rises from the chemical solution container and moves to the next chemical solution container. However, the chemical solution cannot be removed sufficiently in the conventional staining apparatus. Therefore, the remaining chemical solution of the previous cycle mixes into the next chemical solution container and the composition of the chemical solution changes gradually, thus affecting the result of staining. To solve this problem, the chemical solution must be renewed frequently. As a result, the staining apparatus is at rest while the chemical solution is renewed, and the rate of operation of the apparatus drops.

Problem (4)

Since the shape and dimension of the slide holder basket for staining are different from those of the slide holder basket for sealing, it has been necessary to manually taken out the secondary slide glass specimens from the slide holder basket for staining and to mount them again manually with the slide holder basket for sealing. As a result, the efficiency of preparation of the slide specimens is low.

It is therefore a first main object of the present invention to provide an automatic staining apparatus which can automatically attach and remove the basket to and from the clamp member of the automatic staining apparatus so as to solve or mitigate the problem (1) described above.

It is another object of the present invention to provide a novel staining apparatus which can remove sufficiently the chemical solution from the basket after the chemical solution treatment so as to solve or mitigate the problem (3).

It is still another object of the present invention to provide a novel slide holder basket which can eliminate the necessity of withdrawal and rearrangement between the staining step and the sealing step and can automatically attach and remove the basket to and from the clamp member of the automatic staining apparatus so as to solve or mitigate the problem (4).

It is a second main object of the present invention to provide a novel automatic staining apparatus which has a high rate of operation and can stain a large number of slide specimens within a short period of time so as to solve or mitigate the problem (2).

SUMMARY OF THE INVENTION

The first main object of the present invention described above can be accomplished by an automatic staining apparatus for slide specimens as defined in claim 1 of the appended claims.

Thus the automatic staining apparatus of the present invention is an automatic staining apparatus for use in staining a large number of slide specimens by dipping them sequentially into a large number of chemical solutions while they are mounted in a slide holder basket, which comprises:

- a clamp member of the automatic staining apparatus for moving up and down and to the right and left the slide holder basket upon engagement therewith;
- the clamp member consisting of:
- (1) a claim member board;
- (2) finger receiving plates, each fixed to the right or left end of the clamp member board to project therefrom, and having finger receiving holes which fit to a finger tip portion;
- (3) two fingers, each disposed movably to the right and left inside the finger receiving plate below the clamp member board, having the finger tip portions projecting outward and forming a pair with each of the finger receiving plates; and
- (4) an automatic finger driving mechanism for moving the tow fingers towards and away from the finger receiving plates in the interlocking arrangement with each other;
- at least one loading port;
- at least one discharge port; and
- the slide holder basket for slide specimens, having engagement members on the right and left upper side surfaces thereof;
- the engagement members each capable of automatically engaging with, and disengaging from, the clamp member of the staining apparatus;
- the upper end portion of each of the engagement members being spaced apart at a given distance from the side surface of the slide holder basket, and being positioned between each of the fingers and the finger receiving plates of the clamp member when the clamp member of the staining apparatus is in a released state;
- the upper end portion of each of the engagement members having a through-hole having a shape and dimension such that the tip of the finger passes therethrough with a necessary clearance;
- the tip of each of the fingers extending from the finger thereinside through the through-hole to a fitting hole of the finger receiving plate and engaging completely with the clamp member;
- wherein when the clamp member and the slide holder basket start engaging with each other, the upper end portions of the two right and left engagement members, which are positioned at said loading port of said automatic staining apparatus or a relay station, are positioned between the fingers and the finger receiving plates, respectively; next, when the fingers approach to the finger receiving plates, the tip portions of the fingers pass through the through-holes disposed at the upper end portions and fit into the finger receiving holes of the finger receiving plates, thereby engaging the clamp member completely with the slide holder basket; when the slide holder basket is disengaged from the clamp member, the slide holder basket reaches the relay station or the discharge port of the automatic staining apparatus; and then the fingers move away from the finger receiving plates to the positions where the finger tip portions do not come into contact with the upper end portions of the engagement members, thereby completely disengaging the slide holder basket from the clamp member.

Preferred embodiments of the first invention are set forth in claims 2 through 7 of the appended claims. The objects of the invention described above can be accomplished by them.

The second main object of the invention can be accomplished by an automatic staining apparatus for slide specimens in accordance with the second invention of the present invention.

Thus the automatic staining apparatus of the second invention of the present invention is an automatic staining apparatus for use in staining a large number of slide specimens by dipping them sequentially into a large number of chemical solutions while they are mounted in a slide holder basket, which comprises:

- n (an integer of 2 or more) clamp members of the automatic staining apparatus for moving up and down and to the right and left the slide holder baskets upon engagement therewith;
- each of the clamp members consisting of:
- (1) a clamp member board;
- (2) finger receiving plates, each fixed to the right or left end of the clamp member board to project therefrom, and having finger receiving holes which fit to a finger tip portion;
- (3) two fingers, each disposed movably to the right and left inside the finger receiving plate below the clamp member board, having the finger tip portion projecting outward and forming a pair with each of the finger receiving plates; and
- (4) an automatic finger driving mechanism for moving the two fingers towards and away from the finger receiving plates in the interlocking arrangement with each other;
- (n−1) relay stations;

at least one loading port;
at least one discharge port; and
the slide holder basket for slide specimens,
having engagement members on the right and left upper side surfaces thereof;
the engagement members, each capable of automatically engaging with, and disengaging from, the clamp members of the staining apparatus;
the upper end portion of each of the engagement members being spaced apart at a given distance from the side surface of the slide holder basket, and being positioned between each of the fingers and the finger receiving plates of the clamp member when the clamp member of the staining apparatus is in a released state;
the upper end portion of each of the engagement members having a through-hole having a shape and dimension such that the tip of the finger passes therethrough with a necessary clearance;
the tip of each of the fingers extending from the finger thereinside through the through-hole to a fitting hole of the finger receiving plate and engaging completely with the clamp member;
wherein when the clamp member and the slide holder basket start engaging with each other, the upper end portions of the two right and left engagement members, which are positioned at said loading port of said automatic staining apparatus or said relay station, are positioned between the fingers and the finger receiving plates, respectively; next, when the fingers approach to the finger receiving plates, the tip portions of the fingers pass through the through-holes disposed at the upper end portions and fit into the finger receiving holes of the finger receiving plates, thereby engaging the clamp member completely with the slide holder basket; when the slide holder basket is disengaged from the clamp member, the slide holder basket reaches the relay station or the discharge port of the automatic staining apparatus; then, the fingers move away from the finger receiving plates to the positions where the finger tip portions do not come into contact with the upper end portions, thereby completely disengaging the slide holder basket from the clamp member; the (n−1) relay stations are disposed between a large number of chemical solution containers in order to mount temporarily the slide holder basket; and the first of the clamp members is in charge of staining in the zone ranging from the loading port of the automatic staining apparatus to the first of the relay stations, the i-th of the clamp members is in charge of staining in the zone ranging from the (i−1)th of the relay stations to the i-th of the replay stations (with the proviso that $2 \leq i \leq n-1$) and the n-th of the clamp members is in charge of staining in the zone ranging from the (n−1)th of the replay stations to the discharge port in order to stain the n slide holder baskets substantially at the same time and independently with one another.

The second invention has at least two clamp members of the first invention, stains at least two slide holder baskets at the same time by operating these clamp members in the interlocking arrangement and relays automatically the slide holder basket at a specified relay station. These are main features of the second invention. The preferred forms of the second invention are set forth in claims 9 through 14 of the appended claims.

BRIEF DESCRIPTION OF THE DRAWINGS

FIGS. 1 through 6 show embodiments of the automatic staining apparatus of the present invention, wherein:

FIG. 1 is a perspective view of the automatic staining apparatus;

FIG. 2(a) is a perspective view of a slide holder basket of the automatic staining apparatus of the present invention;

FIG. 2(b) shows a support member;

FIG. 3 shows the slide holder basket and a clamp member immediately before engagement or immediately after release;

FIG. 4(a) shows the slide holder basket and the clamp member during engagement or immediately before release;

FIG. 4(b) shows an engagement member when viewed from a side;

FIG. 6 is a schematic view when two robots having the clamp member are operated at the same time;

DESCRIPTION OF THE PREFERRED EMBODIMENTS

Hereinafter, preferred embodiments of the present invention will be described with reference to the accompanying drawings.

EXAMPLE A

Figure 1:
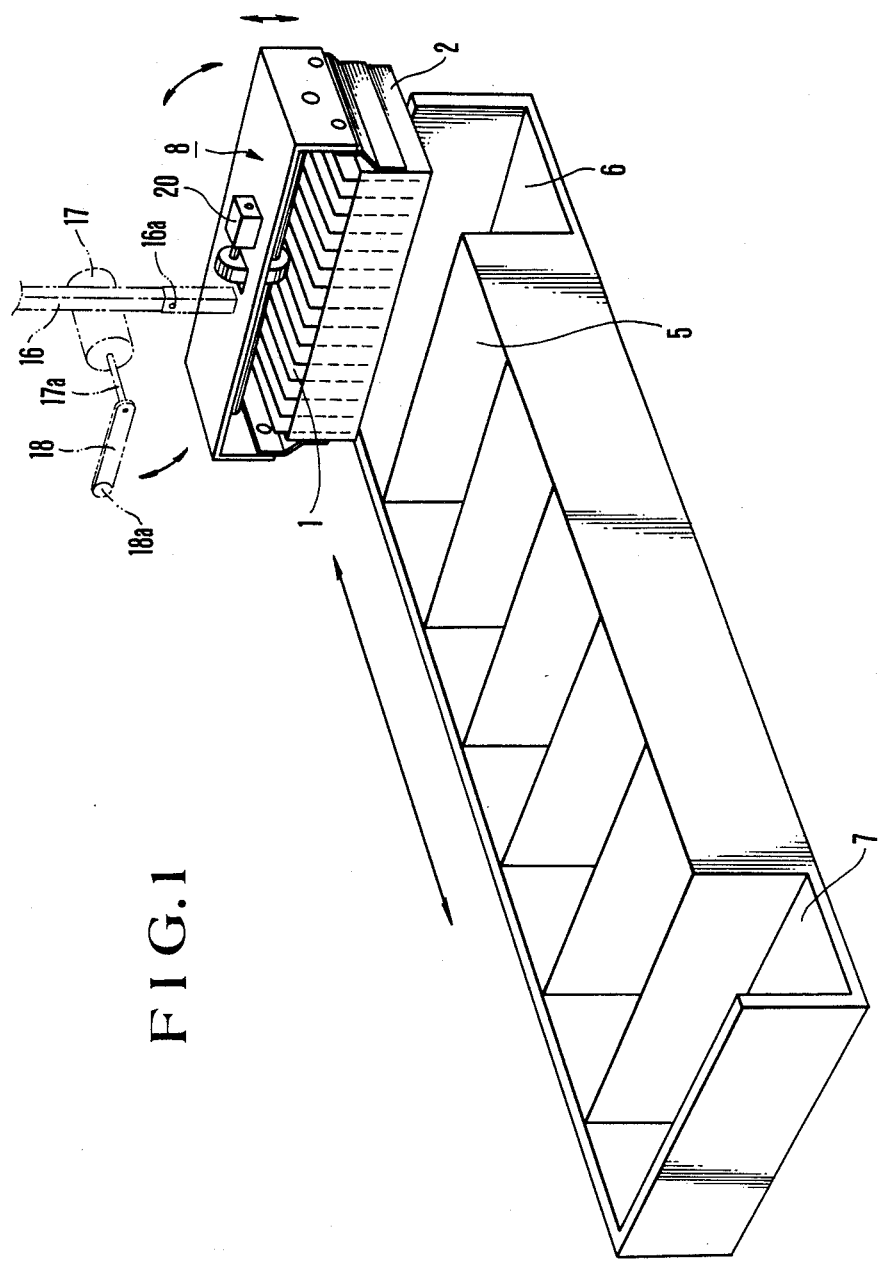

FIG. 1 is a schematic view of the automatic staining apparatus of this embodiment. The apparatus has at its right end a loading port 6 for loading a slide holder basket 2 wherein primary slide specimens 1 to be stained are mounted, and a large number of chemical solution containers 5 are aligned with the loading port 6 in a transverse direction. (In FIG. 1, the number of chemical solution containers is smaller than the actual number.) A chemical solution such as xylene, alcohol, Carazzi hematoxylin, distilled water, etc. is placed in each chemical solution container depending on the object of staining. A discharge port 7 for withdrawing the slide holder basket after the completion of staining is disposed at the left end of the apparatus.

The automatic staining apparatus of the present invention has the slide holder basket 2, and an example of this basket will now be described in detail. FIG. 2 is a perspective view of an example of the slide holder basket 2. Grooves 33 are formed on the front surface 31 and the back 32 in order to mount a large number of slide specimens 1 in parallel with one another with specified spaces between them. A support member 35 is disposed on the bottom 34 in order to prevent the slide specimen 1 from falling from the slide holder basket and to obtain necessary mechanical strength of the slide holder basket (see FIG. 2(b)). This support member 35 may be provided with teeth 36 corresponding to the grooves 33 on the front surface 31 and the back 32 (see FIG. 2(b)) or may have a straight shape without any teeth. In the latter case, too, the slide specimens can be held equidistantly and in parallel with one another by the grooves on the front surface and the back. Engagement members 37, each automatically engaging with and disengaging from a clamp member 8 of the staining apparatus of the present invention are fixed on the right and left side surfaces of the apparatus. The upper end portion 37a of this engagement member 37 is formed at a given distance from the side surface and a through-hole 37b having a sufficient size such that the tip of a finger of the clamp member (12a in FIG. 3) can pass therethrough when the clamp member is in engagement is formed on the engagement member 37. Therefore, automatic engagement and disengagement between the upper end portion 37a and the clamp member 8 of the automatic staining apparatus become possible and the falling of the slide holder basket from the clamp member 8 during engagement can be prevented.

There is no particular limitation to the material of the slide holder basket. Any material may be used so long as it does not cause any chemical reaction with a staining solution and a sealing agent. From the aspect of the cost etc., it is preferred to use SUS 304 stainless steel or Teflon.

In the example of the slide holder basket, its shape and dimension are substantially the same as those of ordinary slide holder baskets for sealing. Accordingly, it is no longer necessary at all to withdraw the slide specimens between the staining step and the sealing step and to put them in another sealing basket.

Next, the engaging and disengaging operations between the clamp member 8 and the slide holder basket 2 will be described. An operator can put the slide holder basket 2 to the loading port 6 irrespective of the present position of the clamp member 8. When the clamp member 8 comes above the loading port 6, the clamp member 8 lowers automatically and the finger 12 of each clamp member 8 comes inside the upper end portion 37a of each engagement member 37 of the slide holder basket 2 while a finger receiving plate 13 of the clamp member 8 comes outside the upper end portion 37a. The clamp member 8 stops there. Subsequently, the finger 12 moves toward the finger receiving plate 13 at that position and the finger tip 12a passes through the through-hole 37b of the upper end portion 37a and engages with a finger receiving hole 13a bored on the finger receiving plate 13. Thus the clamp member 8 and the slide holder basket 2 engage with each other completely. FIG. 4 shows this situation.

FIGS. 3 and 4 exemplify this clamp mechanism. The finger receiving plate 13 is fixed to a clamp member board 11 and the finger 12 is screwed to a screw portion 14a of a rotary shaft 14. This rotary shaft 14 is in turn supported pivotally by the finger receiving plate 13. This screw portion 14a is threaded in the opposite directions at its right and left portions. (For example, if the screw portion on the right side is a clockwise screw, the screw portion on the left side is an anti-clockwise screw.) Therefore, when the rotary shaft 14 is rotated, the right and left fingers 12 move towards the finger receiving plate 13, respectively, and when the rotary shaft 14 is rotated in the reverse direction, on the contrary, the fingers 12 move away from the finger receiving plate 13, respectively. The rotary shaft 14 is rotated by transmitting the rotary force of a motor 20 through a belt 15.

While kept in engagement, the clamp member 8 and the slide holder basket 2 are moved above a specified chemical solution container 5 and are then lowered so that the slide specimens 1 are dipped into the chemical solution for a given period while being shaken up and down. After the treatment is complete, the clamp member 8 and the slide holder basket 2 rise. The clamp member 8 is preferably shaken up and down during dipping because the chemical solution treatment becomes uniform.

Figure 5A:
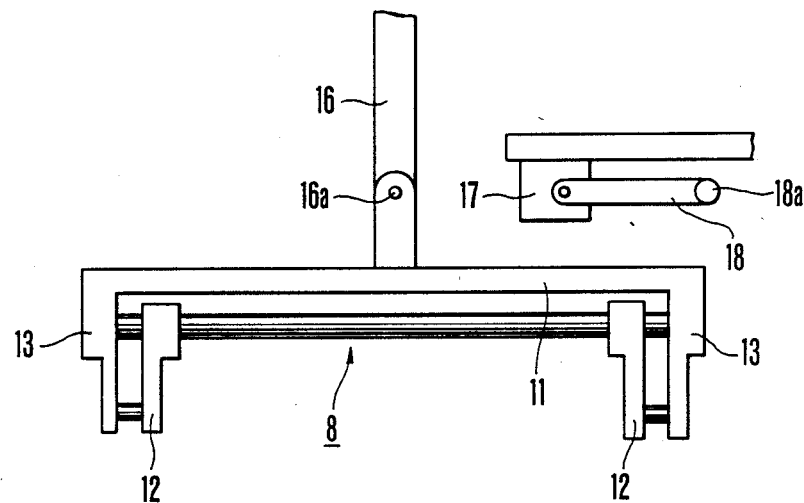
FIGS. 5a and 5b are explanatory views of a mechanism for inclining the clamp member.
Figure 5B:
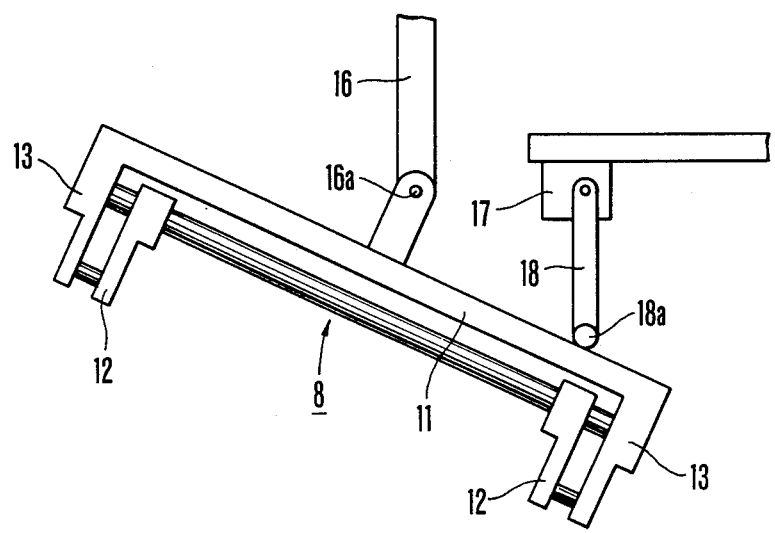
Figure 8:
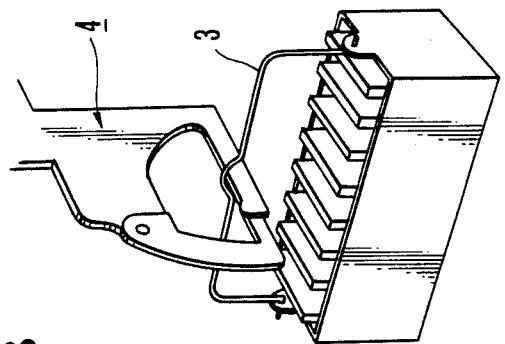
FIG. 8 is a perspective view of a conventional basket for staining and a clamp member.
Figure 7:
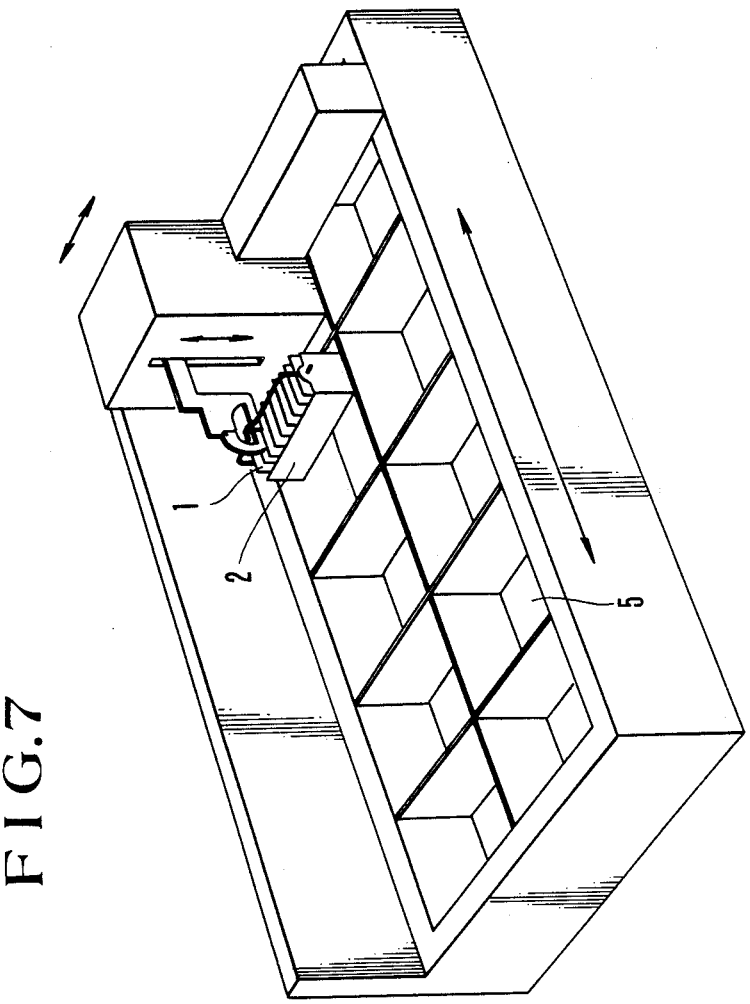
FIG. 7 is a perspective view of a conventional automatic staining apparatus.

When the clamp member 8 is raised and tilted, it becomes possible to shake off the chemical solution adhering to the slide specimen etc. therefrom, and this is preferable because degradation of the chemical solution in the next chemical solution container can be prevented. The basket tilting mechanism used in this embodiment (the portion represented by dash lines in FIG. 1) will be described with reference to FIGS. 5a and 5b. The clamp member 8 can rotate only around a rotation node 16a and is supported by a rotary joint 16. A motor 17 is fixed above the clamp member board 11. An arm 18 is fixed to the motor shaft 17a (see FIG. 1) and can rotate at a specified angle around the motor shaft 17a. Normally, the arm 18 is out of contact with the clamp member board 11 (FIG. 5a). When, however, the arm 18 is rotated by the motor 17, the arm 18 comes into contact with the clamp member board 11, pushes down the contact portion and rotates the clamp member 8 around the rotation node 16a of the rotary joint 16, thereby tilting the clamp member 8 (FIG. 5b). Preferably, a cam follower 18a is fitted to the tip of the arm in order to reduce friction and to make rotation smooth. The angle of inclination of the clamp member can be varied by the position of the motor 17, the position of the rotation node 16a of the rotary joint 16 and the length and rotation angle of the arm 18. An angle of inclination of 20° to 45° will suffice It is also possible to control driving of the motor so as to keep the clamp member for a given period when it reaches the maximum tilting angle. It is also possible to drive it specifically from an inclined state. The chemical solution can be removed sufficiently by keeping the clamp member for a given period in a state of the maximum tilting angle or by inclining it from the horizontal posture to the maximum tilting angle and then decreasing the tilting angle and inclining it again to the maximum tilting angle. When the motor 17 is rotated reversely after inclination, the arm 18 moves away from the clamp member board 11 and the clamp member 8 returns to the horizontal posture.

Unlike the prior art technique, since the basket is engaged with the clamp member at the upper end portions of the right and left engagement members in this embodiment, the basket can be inclined automatically.

While the engagement between the clamp member 8 and the slide holder basket 2 is kept, they are moved above a specified chemical solution container 5 and are then lowered so that the slide specimens 1 are dipped into the chemical solution for a given time. After the chemical solution treatment is completed, the basket moves over the chemical solution container 5, stops temporarily and then inclines the basket 2 to remove or cut off sufficiently the chemical solution.

After the completion of staining, the clamp member 8 comes above the discharge port 7 and then lowers so that the slide holder basket 2 stops at the position where its bottom surface comes into contact with the bottom plate of the discharge port 7. Then, the clamp member 8 is released from the engagement automatically by the automatic engagement mechanism, rises while leaving the slide holder basket 2 at the discharge port 7 and returns to a predetermined position.

It is no longer necessary for the operator to stand by when the slide holder basket is attached to and removed from the clamp member as has been necessary in the prior technique. Therefore, there is no waiting time for the operator as well as for the staining apparatus, and the rate of operation can be improved and the load to the operator can be reduced.

EXAMPLE B

Next, the second embodiment of the present invention will be described with reference to FIG. 6.

At least two robots (only first and second robots 21 and 22 are shown in the drawing) are moved to the right and left by a transverse driving mechanism consisting of a guide rail 23, a feed screw 24 and an X-axis motor 25. It is possible to readily modify the mechanism so that at least tow robots can be driven independently by use of at least two independent driving mechanisms.

The first and second robots 21, 22 each have the clamp member 8 and the vertical driving mechanism. The vertical driving mechanism has a feed screw 26 and a Y-axis motor 27.

Twenty-three chemical solution containers (#1–#23) are aligned transversely between the loading port and the discharge port, and the place where the slide holder basket 2 is placed temporarily (hereinafter referred to as the "relay station 19") is disposed between the chemical solution containers #10 and #12. The position of the relay station can be changed in accordance with a program. This relay station may be either the chemical solution container containing therein the chemical solution or an empty place.

The first robot 21 is in charge of the zone ranging from the loading port 6 to the relay station 19 and the second robot 22 is in charge of the zone ranging from relay station 19 to the discharge port 7.

When the chemical solution treatment of #10 is completed, the first clamp member 8 comes above the relay station 19, then lowers and releases automatically the basket 2 while the bottom surface of the slide holder basket 2 is grounded on the relay station 19.

After leaving the basket 2 at the relay station 19, the first robot moves to the loading port 6 in order to treat the next new basket. Meanwhile the second robot 22 comes above the relay station, then lowers and automatically engages with the basket 2 on the relay station 19. Thereafter, the chemical solution treatment of #12 et seqq. are carried out. When all of the chemical solution treatments are over, the second robot 22 releases automatically the basket 2 at the discharge port 7 and then returns to the relay station 19 in order to engage with the next basket at the relay station. In this manner, staining can be carried out for the two baskets at the same time and independently with each other by use of the firs and second robots 21 and 22. Therefore, the rate of operation of the staining apparatus is substantially doubled.

What is claimed is:

1. An automatic staining apparatus for use in staining a large number of slide specimens by dipping them sequentially into a large number of chemical solutions while they are mounted in a slide holder basket, said apparatus comprising:
   a clamp member of said automatic staining apparatus for moving up and down and to the right and left, said slide holder basket upon engagement therewith;
   said clamp member comprises:
   (1) a clamp member board having a right and left end;
   (2) two finger receiving plates, each fixed to the right end and left end respectively of said clamp member board to project therefrom, and having a finger receiving hole which fits to a finger tip portion;
   (3) two fingers, each disposed movably to the right or left inside said finger receiving plate below said clamp member board, having said finger tip portion projecting outward and forming a pair with each of said finger receiving plates; and
   (4) an automatic finger driving mechanism for moving said two fingers towards and away from said finger receiving plates in the interlocking arrangement with each other;
   at least one loading port;
   at least one discharge port; and
   said slide holder basket for slide specimens, having engagement members on right and left upper side surfaces thereof;
   said engagement members each capable of automatically engaging with, and disengaging from, said clamp member of said staining apparatus;
   the upper end portion of each of said engagement members being spaced apart at a given distance from the side surface of said slide holder basket, and being positioned between each of said fingers and said finger receiving plates of said clamp member when said clamp member of said staining apparatus is in a released state;
   the upper end portion of each of said engagement members having a through-hole having a shape and dimension such that the tip of said finger passes therethrough with a necessary clearance;
   said tip of each of said fingers extending from said finger thereinside through said through-hole to a fitting hole of said finger receiving plate and engaging completely with said clamp member.

2. The automatic staining apparatus for slide specimens as in claim 1, wherein said slide holder basket for slide specimens has substantially the same size as ordinary slide holder baskets for sealing.

3. The automatic staining apparatus for slide specimens as defined in claim 1, which further comprises a tilting mechanism for tilting said clamp member above said chemical solutions.

4. The automatic staining apparatus for slide specimens as in claim 3, wherein said slide holder basket for slide specimens has substantially the same size as ordinary slide holder baskets for sealing.

5. The automatic staining apparatus for slide specimens as defined in claim 3, wherein the maximum tilting angle of said clamp member and said slide holder basket is from about 20° to about 45°.

6. The automatic staining apparatus for slide specimens as claim 5, wherein said slide holder basket for slide specimens has substantially the same size as ordinary slide holder baskets for sealing.

7. The automatic staining apparatus for slide specimens as defined in claim 3, wherein said tilting mechanism comprises:
   (1) a rotary joint supporting said clamp member from above and capable of rotating around a rotation node;
   (2) a motor disposed above said clamp member; and
   (3) an arm having one of the end thereof fixed to a motor shaft.

8. The automatic staining apparatus for slide specimens as in claim 7 wherein the maximum tilting angle of said clamp member and slide holder basket is from about 20° to about 45°.

9. The automatic staining apparatus for slide specimens as in claim 7, wherein said slide holder basket for slide specimens has substantially the same size as ordinary slide holder baskets for sealing.

10. The automatic staining apparatus for slide specimens as defined in claim 7 further including means for providing inclination of said clamp member and said slide holder basket after they are inclined form the horizontal posture to the maximum tilting angle so that they are again tiled to the maximum tilting angle by reducing the tilting angle.

11. The automatic staining apparatus for slide specimens as in claim 10 wherein the maximum tilting angle of said clamp member and said slide holder basket is from about 20° to about 45°.

12. The automatic staining apparatus for slide specimens as defined in claim 3 further including means for providing inclination of said clamp member and said slide holder basket after they are inclined from the horizontal posture to the maximum tilting angle so that they are again tilted to the maximum tilting angle by reducing the tilting angle.

13. The automatic staining apparatus for slide specimens as in claim 12 wherein the maximum tilting angle of said clamp member and said slide holder basket is from about 20° to about 45°.

14. The automatic staining apparatus for slide specimens as claim 12, wherein said slide holder basket for slide specimens has substantially the same size as ordinary slide holder baskets for sealing.

15. The automatic staining apparatus for slide specimens as in claim 1, wherein said automatic finger driving mechanism comprises:
  (1) a rotary shaft supported rotatably between said two finger receiving plates and having two screw portions at both ends thereof which are threaded in mutually apposite directions; and
  (2) a motor for rotating said rotary shaft either directly or indirectly through a belt.

16. The automatic staining apparatus for slide specimens as in claim 15, wherein said slide holder basket for slide specimens has substantially the same size as ordinary slide holder baskets for sealing.

17. The automatic staining apparatus for slide specimens as defined in claim 15, which further comprises a tilting mechanism for tilting said clamp member above said chemical solutions.

18. The automatic staining apparatus for slide specimens as in claim 17 wherein the maximum tilting angle of said clamp member and said slide holder basket is from about 20° to about 45°.

19. The automatic staining apparatus for slide specimens as defined in claim 17 further including means for providing inclination of said clamp member and said slide holder basket after they are inclined from the horizontal posture to the maximum tilting angle so that they are again tilted to the maximum tilting angle by reducing the tilting angle.

20. The automatic staining apparatus for slide specimens as in claim 19 wherein the maximum tilting angle of said clamp member and said slide holder basket is from about 20° to about 45°.

21. The automatic staining apparatus for slide specimens as defined in claim 17, wherein said tilting mechanism comprises:

(1) a rotary joint supporting said clamp member from above and capable of rotating around a rotation node;
(2) a motor disposed above said clamp member; and
(3) an arm having one of the end thereof fixed to a motor shaft.

22. The automatic staining apparatus for slide specimens as in claim 21 wherein the maximum tilting angle of said clamp member and said slide holder basket is from about 20° to about 45°.

23. The automatic staining apparatus for slide specimens as defined in claim 21 further including means for providing inclination of said clamp member and said slide holder basket after they are inclined from the horizontal posture to the maximum tilting angle so that they are again tilted to the maximum tilting angle by reducing the tilting angle.

24. The automatic staining apparatus for slide specimens as in claim 23 wherein the maximum tilting angle of said clamp member and said slide holder basket is from about 20° to about 45°.

25. The automatic staining apparatus for use in staining a large number of slide specimens by dipping them sequentially into a large number of chemical solutions while they are mounted in a slide holder basket, said apparatus comprising:
  n (an integer of 2 or more) clamp members of said automatic staining apparatus for moving up and down and to the right and left said slide holder basket upon engagement therewith;
  each of said clamp members comprises:
    (1) a clamp member board;
    (2) two finger receiving plates, each fixed to the right end and left end respectively of said clamp member substrate to project therefrom, and having a finger receiving hole which fits to a finger tip portion;
    (3) two fingers, each disposed movably to the right and left inside said finger receiving plate below said clamp member board, having said finger tip portion projecting outward and forming a pair with each of said finger receiving plates; and
    (4) an automatic finger driving mechanism for moving said two fingers towards and away from said finger receiving plates in the interlocking arrangement with each other;
  (n−1) relay stations;
  at least one loading port;
  at least one discharge port; and
  said slide holder basket for slide specimens, having engagement members on the right and left upper side surfaces thereof;
    said engagement members each capable of automatically engaging with, and disengaging from, said clamp members of said staining apparatus;
    the upper end portion of each of said engagement members being spaced apart at a given distance from the side surface of said slide holder basket, and being positioned between each of said fingers and said finger receiving plates of said clamp member when said clamp member of said staining apparatus is in a released state;
    the upper end portion of each of said engagement members having a through-hole having a shape and dimension such that the tip of said finger passes therethrough with a necessary clearance;

said tip of each of said fingers extending from said finger thereinside through said throughhole to a fitting hole of said finger receiving plate and engaging completely with said clamp member; said (n−1) relay stations are disposed between a large number of chemical solution containers in order temporarily said slide holder basket; and the first of said clamp members moves from said loading port of said automatic staining apparatus to the first of said relay stations, the i-th of said clamp members moves from the (i−1)th of said relay stations to the i-th of said relay stations (with the proviso that $2 \leq i \leq n-1$) and the n-th of said clamp members moves from the (n−1)th of said relay stations to said discharge port in order to stain said n slide holder baskets substantially at the same time and independently with one another.

26. The automatic staining apparatus for slide specimens as in claim 25 wherein said slide holder basket for slide specimens has substantially the same size as ordinary slide holder baskets of sealing.

27. The automatic staining apparatus for slide specimens as in claim 25, wherein said automatic finger driving mechanism comprises:
   (1) a rotary shaft supported rotatably between said two finger receiving plates and having two screw portions at both ends thereof which are threaded in mutually opposite directions; and
   (2) a motor for rotating said rotary shaft either directly or indirectly through a belt.

28. The automatic staining apparatus for slide specimens as in claim 27 wherein said slide holder basket for slide specimens has substantially the same size as ordinary slide holder baskets of sealing.

29. The automatic staining apparatus for slide specimens as defined in claim 25 or 27, which further comprises a tilting mechanism for tilting said clamp member above said chemical solutions.

30. The automatic staining apparatus for slide specimens as in claim 29 wherein said slide holder basket for slide specimens has substantially the same size as ordinary slide holder baskets of sealing.

31. The automatic staining apparatus for slide specimens as in claim 29 wherein the maximum tilting angle of said clamp member and said slide holder basket is from about 20° to about 45°.

32. The automatic staining apparatus for slide specimens as in claim 31 wherein said slide holder basket for slide specimens has substantially the same size as ordinary slide holder baskets of sealing.

33. The automatic staining apparatus for slide specimens as in claim 29, wherein the inclination of said clamp member and said slide holder basket is such that after they are inclined from the horizontal posture to the maximum tilting angle, they are again tilted to the maximum tilting angle by reducing the tilting angle.

34. The automatic staining apparatus for slide specimens as in claim 33 wherein the maximum tilting angle of said clamp member and said slide holder basket is from about 20° to 45°.

35. The automatic staining apparatus for slide specimens as in claim 33 wherein said slide holder basket for slide specimens has substantially the same size as ordinary slide holder baskets of sealing.

36. The automatic staining apparatus for slide specimens as in claim 29, wherein said tilting mechanism comprises:
   (1) a rotary joint supporting said clamp member from above and capable of rotating around a rotation node;
   (2) a motor disposed above said clamp member; and
   (3) an arm having one of the ends thereof fixed to a motor shaft.

37. The automatic staining apparatus for slide specimens as in claim 36 wherein the inclination of said clamp member and said slide holder basket is such that after they are inclined from the horizontal posture to the maximum tilting angle, they are again tilted to the maximum tilting angle by reducing the tilting angle.

38. The automatic staining apparatus for slide specimens as in claim 36 wherein the maximum tilting angle of said clamp member and said slide holder basket is from about 20° to 45°.

39. The automatic staining apparatus for slide specimens as in claim 36 wherein said slide holder basket for slide specimens has substantially the same size as ordinary slide holder baskets of sealing.

* * * * *